United States Patent [19]

Poyner et al.

[11] Patent Number: 5,600,012
[45] Date of Patent: Feb. 4, 1997

[54] PROCESS FOR PRODUCING TETRAHYDROISOALPHA ACIDS

[75] Inventors: William R. Poyner, Crossway Green; Geoffrey Smith, Brierly Hill; Keith T. Westwood, Bodenham, all of United Kingdom; David W. Hysert, Yakima, Wash.

[73] Assignee: John I. Haas, Inc., Yakima, Wash.

[21] Appl. No.: 417,984

[22] Filed: Apr. 6, 1995

[51] Int. Cl.$^6$ .................................................. C07C 45/67
[52] U.S. Cl. ........................... 568/347; 568/350; 426/600
[58] Field of Search .................................... 568/347, 350; 426/600

[56] References Cited

U.S. PATENT DOCUMENTS

| | | | |
|---|---|---|---|
| 3,044,879 | 7/1962 | Koch et al. | 99/50.5 |
| 3,923,897 | 12/1975 | Worner | 568/347 |
| 4,644,084 | 2/1987 | Cowles et al. | 568/341 |
| 4,767,640 | 8/1988 | Goldstein et al. | 426/600 |
| 4,778,691 | 10/1988 | Todd et al. | 426/600 |
| 5,013,571 | 5/1991 | Hay | 426/600 |
| 5,296,637 | 3/1994 | Stegink et al. | 568/347 |

OTHER PUBLICATIONS

Bruce A. Hay and John W. Homiski: Efficient One–Step Preparation of the Beer Additive Tetrahydroisoα–Acids (1991) (pp. 1732–1734).

P. Margaret Brown, G. A. Howard, and A. R. Tatchell: Chemistry of Hop Constituents. Part XIII. The Hydrogenation of Isohumulone. (1959) (pp. 545–551).

Eiichi Kobuko and Yoshiro Kuroiwa: Tetrahydrohumulones as a New Source of Bitter Flavor in Brewing. (1968) (pp. 33–42).

W. J. G. Donnelly and P. V. R. Shannon: cis– and trans–Tetrahydroisohumulones. (1970) (pp. 524–530).

G. A. Howard, C. A. Slater, A. R. Tatchell: Brewing Industry Research Foundation. (1957) (pp. 237–248).

M. Verzele and D. De Keukeleire: Chemistry and Analysis of Hop and Beer Bitter Acids. (1991) (pp. 126–138).

M. Verzels: Centenary Review, 100 Years of Hop Chemistry and its Relevance to Brewing. (1986) (pp. 32–48).

M. Verzele, H. E. Jansen, and A. Ferdinandus: Organoleptic Trials with Hop Bitter Substances. (1970) (pp. 25–28).

*Primary Examiner*—James H. Reamer
*Attorney, Agent, or Firm*—Miller, Nash, Wiener, Hager & Carlsen

[57] ABSTRACT

Tetrahydro-iso-α-acids ("THIAA") are prepared directly from iso-α-acids ("IAA") by hydrogenation. Free IAA are first dissolved in ethanol. The solution is then hydrogenated in the presence of a particular type of noble metal catalyst. Hydrogenation is controlled naturally by the reaction between the catalyst and the IAA so that the IAA will be selectively converted to THIAA without unacceptable perhydrogenation into other forms.

9 Claims, No Drawings

PROCESS FOR PRODUCING TETRAHYDROISOALPHA ACIDS

TECHNICAL FIELD

The invention disclosed here generally relates to processes for making beer additives from hop extracts. More particularly, it relates to processes for making tetrahydroisoalpha acids ("tetrahydro-iso-α-acids").

BACKGROUND ART

If exposed to light, beer is known to develop a "light struck" or "skunky" flavor. This is due to the light sensitivity of the conventional hop bittering substances which make up an essential ingredient of beer. The invention disclosed here relates to the production of tetrahydro-iso-α-acids. Tetrahydro-iso-α-acids are well-known as bittering agents derived from hops. However, they are insensitive to light and may be used to brew beer that will not subsequently develop a skunky flavor. Before the invention claimed here is described and explained, it will be helpful to first provide a brief history of hop usage in the brewing industry.

I. Historical Background

It is believed that hops were initially used solely as a preservative agent when beer brewing evolved into an industry centuries ago. At that time, refrigeration did not exist and a need arose to lengthen the storage life of beer. The bitter taste and flavor created by hopped beer eventually gained popularity in and of itself, independent of storage considerations.

The hop taste of beer comes from components contained in the lupulin glands of the hop cones. Lupulin glands have two important bittering substances: alpha acids ("α-acids") and beta acids ("β-acids"), which are sometimes called humulones and lupulones, respectively. Isomerized versions of α-acids ("iso-α-acids") are the predominant bittering agent in beer.

Conventional beer brewing involves introducing and boiling leaf hops in a brew kettle. Boiling causes isomerization of the α-acids as they are extracted from the lupulin. The isomerized acids, or iso-α-acids, are more bitter than α-acids and have a higher degree of solubility in beer.

To a large extent, the efficiency of hop utilization in commercial beer-making has depended on the degree to which iso-α-acids are converted from α-acids. Using conventional brewing methods, it has been estimated that the utilization rate of the α-acids in the lupulin glands is 25%–30%.

Although the cost of hops makes up a small part of the overall cost of producing beer, it is nevertheless significant in absolute terms. In the J.Inst. Brew., January-February, 1986, Vol. 92, pp. 32–48, M. Verzele estimated the total worldwide hop usage per year to be about 100,000 tons having a value, at the time, of 100–300 million English pounds. Hop usage is much higher today. What this means is that the cost of hops for a large brewery is not insignificant, and finding ways to make hop utilization more efficient can result in worthwhile cost savings.

Hops are harvested once a year. During harvest, they are dried and compressed into large bales for sale to breweries or hop processors. The lupulin glands in baled hop cones initially contain unconverted α-acids.

If baled hops are stored at ambient conditions for a long period, the α-acids begin to oxidize and polymerize into a hard resin. Not only will this affect the efficiency of subsequent conversion into iso-α-acids, when the hops are subsequently used to brew beer, but it also creates other undesirable by-products during the brewing process.

Iso-α-acids are less prone to deterioration in comparison to α-acids. Consequently, rather than store baled hops, processes have been developed to extract and convert α-acids into pure iso-α-acids that may be stored in extract form for later use. Extracts of iso-α-acids remain stable for a relatively long period of time.

The benefits are at least two-fold: First, having a bittering agent that is stable means that it is easier to brew beer that is consistent in taste. In the past, brewers had to be concerned about changes in the potency of baled hops after extended periods of storage and how such changes affected taste. Extracts of iso-α-acids significantly reduce this problem. Second, extraction and isomerization processes have evolved and improved over time, resulting in more efficient conversion of α to iso-α-acids. This has resulted in a larger effective quantity of usable bittering agent per pound of hops harvested. Obviously, this can result in significant cost savings for brewers.

II. The Development of Tetrahydro-iso-α-acids

Although generally less prone to deterioration than pure α-acids, iso-α-acids are nevertheless chemically sensitive to light. This is what causes beer to develop the "skunky" flavor mentioned above. As a result, beer is traditionally bottled in dark brown glass to protect it against light exposure.

It has long been known that it is possible to produce derivatives of iso-α-acids known as tetrahydro-iso-α-acids. Tetrahydro-iso-α-acids are (1) more potent as a bittering agent; (2) have the advantage of being less sensitive to changes in light and temperature; and (3) provide enhanced beer-foaming characteristics. All of these characteristics have led to a growing demand by brewers to use tetrahydro-iso-α-acids in brewing beer. However, low light sensitivity may be the predominant reason for using them, because it enables brewers to package beer in clear or green glass bottles.

In an informative article entitled, "Efficient One-Step Preparation of the Beer Additive Tetrahydroisoalpha-Acids," J. Agric. Food Chem. 1991, 39, 1732–1734, Bruce A. Hay and John W. Homiski ("Hay article") explained what is believed to be all the known methods for producing tetrahydro-iso-α-acids.

One method discussed in the Hay article is disclosed in U.S. Pat. No. 3,522,975, issued to P.H. Todd and L.R. Worden. This patent discloses the synthesis of tetrahydro-iso-α-acids by using the β-acids portion of the lupulin glands. It is a three-step process relying primarily on an oxidation step. The Hay article described this method as inefficient.

A second method discussed in the Hay article involves hydrogenating α-acids as a first step, followed by isomerizing the hydrogenated product into tetrahydro-iso-α-acids. This method was described as problematical, because of the difficulty of controlling hydrogenation. In order to reach tetrahydro-iso- α-acids as an end product, the Hay article described that it was necessary to strictly control the amount of hydrogen used.

The Hay article also discussed a third method newly developed at the time by Messrs. Hay and Homiski. This method is the subject of U.S. Pat. No. 5,013,571, assigned to Pfizer, Inc. ("Pfizer method"). The Pfizer method is a one-step process where α-acids are simultaneously isomerized and hydrogenated to produce tetrahydro-iso-α-acids. The process was described as being very advantageous in terms of being the least expensive way known to produce tetrahydro-iso-α-acids. It is believed the process is currently in use by Pfizer, Inc.

Last, the Hay article discussed producing tetrahydro-iso-α-acids by more or less reversing the sequence of hydrogenation and isomerization in the second method described above. The first or isomerization step involved producing iso-α-acids from α-acids by any one of a known number of methods. The second step involved the hydrogenation of the iso-α-acids. This method, as described by the Hay article, is believed to be the closest in similarity to the invention disclosed here.

Although the Hay article described that several researchers may have used the two-step method described immediately above, including M. Verzele, who is well-known in the field, it was described as having confusing and contradictory results. According to the article, because of the difficulty of isolating and identifying the products of hydrogenation, no one had successfully produced tetrahydro-iso-α-acids in high yield by the simple hydrogenation of iso-α-acids. Messrs. Hay and Homiski stated that they had confirmed this fact in their laboratory, suggesting that it could not be done. The present invention accomplishes the contrary, i.e., it provides for the simple hydrogenation of iso-α-acids into tetrahydro-iso-α-acids and produces tetrahydro-iso-α-acids in good yield with high purity.

The Pfizer process discloses the use of "palladium on carbon" ("Pd/C") as a catalyst. In general terms, the catalyst has a certain amount of active metal (palladium) loaded on a carbon support.

Palladium on carbon catalysts are used for a miscellany of hydrogenation reactions and, in general, different grades or makes of Palladium on a carbon support will achieve approximately equivalent and satisfactory performance. However, the need to modify the activity of a catalyst to suit the specific requirements of certain reactions has long been recognized by catalyst manufacturers and special grades of Palladium catalyst are developed and marketed as a result. By carefully selecting and utilizing a particular Pd/C catalyst, it is possible to create a controlled hydrogenation process where hydrogenation ends naturally, i.e., without resort to physically cutting off the supply of hydrogen, thereby creating pure tetrahydro-iso-α-acids as an end product. How this is accomplished in the context of the invention is explained below.

It should be mentioned that α-acids and β-acids consist of mixtures of acids. For example, α-acids consist of mixtures of humulones, co-humulones, ad-humulones, and other minor constituents. Consequently, α-acids are usually referred to in the plural. Likewise, β-acids consist of mixtures of lupulones, co-lupulones, ad-lupulones, and other minor constituents. The same is true for tetrahydro-iso-α-acids. All of this would be understood by the person skilled in the art. For the sake of clarity, and unless specifically indicated otherwise, if any acid product of lupulin is referred to here in singular form, it is to be understood that plural form variations are included.

SUMMARY OF THE INVENTION

The invention is a process for making pure tetrahydro-iso-α-acids from pure iso-α-acids, in a single step, by hydrogenation. In accordance with the invention, "free" iso-α-acids are dissolved in ethanol. The pH of the ethanol is natural and unadjusted. A noble metal catalyst is added to the solution and the iso-α-acids are hydrogenated. Hydrogenation converts the iso-α-acids into tetrahydro-iso-α-acids.

An important aspect of the invention is that the iso-α-acids are not over-hydrogenated into other forms such as hexahydro-iso-α-acids or octahydro-iso-α-acids. Hydrogenation is controlled because the chemical reaction ends naturally with the production of tetrahydro-iso-α-acids. It is unnecessary to be concerned about stringently controlling or cutting off the supply of hydrogen to end hydrogenation.

Over-hydrogenation ("perhydrogenation") is avoided by allowing hydrogenation to occur at a certain optimal temperature, which is higher than what would be considered normal, and by using catalyst concentrations or catalyst types which promote a high degree of selectivity. In combination, these factors function to stop hydrogenation when the amount of hydrogen required to convert iso-α-acids to tetrahydro-iso-α-acids has been absorbed.

The invention is intended to be used as the second step of a two-step process for producing tetrahydro-iso-α-acids from α-acids. The first step will entail producing iso-α-acids from α-acids (or perhaps, from β-acids) by any number of known processes. The object of the invention is to provide the second step, i.e., produce pure tetrahydro-iso-α-acids from iso-α-acids.

BEST MODE FOR CARRYING OUT THE INVENTION

It is presumed that the skilled person is familiar with iso-α-acids (hereafter "IAA") and knows how IAA can be obtained or made. For example, IAA is presently produced by J.I. Haas, Inc. at its Yakima, Washington facility, and by Hop Developments, Ltd. at its Eardiston, United Kingdom facility. It is also believed to be available from Pfizer, Inc., the Kalamazoo Spice Extraction Company ("Kalsec"), and several other dealers and hop processors. All of these companies are well-known in the brewing industry.

As described above, the invention involves using hydrogenation to produce a high purity yield of tetrahydro-iso-α-acids (hereafter "THIAA") directly from IAA. This is represented at a molecular level by the schematic shown below:

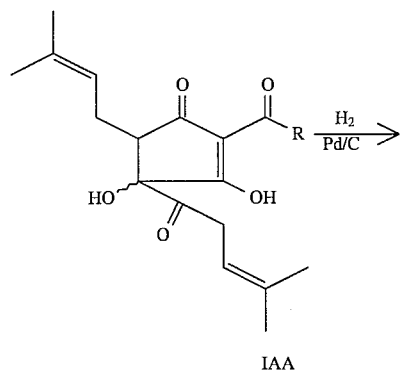

IAA

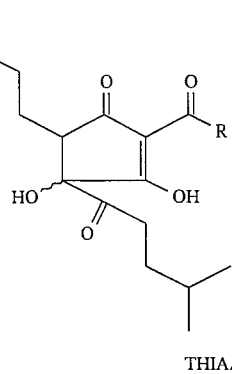

R(typical) = CH$_2$CH(CH$_3$)$_2$, CH(CH$_3$)$_2$, or CH(CH$_3$)CH$_2$CH$_3$

THIAA

The term "H$_2$" above means hydrogenation, which is a well-known process. "Pd/C" means "palladium on carbon," which is well-known as a catalyst, the details of which are further discussed below. Together, the terms as shown mean hydrogenation in the presence of a palladium on carbon catalyst.

Free IAA is known to be substantially soluble in the lower alcohols. In accordance with the invention, free IAA is dissolved in ethanol alcohol ("ethanol") to produce a solution of IAA for subsequent hydrogenation. Since the solvent is ethanol, it is unnecessary to raise the pH of the solution in order to obtain adequate dissolution of IAA, and no buffering or other pH adjustment of the alcoholic solution is necessary. The natural or effective pH of the alcoholic solution is in the order of pH3, although pH is not particularly meaningful when used in connection with alcohol.

By way of comparison, the thrust of U.S. Pat. No. 5,013,571, issued to Hay and Homiski, is to simultaneously isomerize and hydrogenate alpha acid in an aqueous solution at a higher pH. The higher pH is required in order to dissolve and accelerate the isomerization of α-acids in water.

What follows is a series of examples (Examples 1–6) summarizing actual tests which led to the development of the invention. The first three examples (Examples 1–3) are preliminary "proof of concept" tests. Example 1 is illustrative of the difficulties associated with hydrogenating IAA into THIAA. Examples 2 and 3 illustrate the changes which were made in an attempt to overcome certain problems noted in Example 1. These tests were conducted using a particular type of Pd/C catalyst, the description of which follows Examples 1–3.

Examples 4–6 disclose further details in connection with successfully controlling hydrogenation. These tests describe use of an alternative type of Pd/C catalyst, in combination with hydrogenating at higher than normal temperatures. The description of the catalyst, and a comparison of it with the catalyst used in Examples 1–3, follows Examples 4–6. The combination of catalyst and higher than normal temperatures produces what is believed to be unexpected results.

Hydrogenation itself is a process that is well known. Consequently, it is unnecessary to describe the specific details as to how hydrogen is supplied in the following examples, other than the conditions at which hydrogenation occurs.

EXAMPLE 1

A 300 gram solution of free IAA in ethanol was prepared containing 90 grams of IAA. The IAA was obtained from Hop Developments, Ltd. of the United Kingdom and was assayed at 95% purity. A catalyst was added to the solution consisting of 8.0 grams (approximately 8.9% w/w) of 5% Pd/C (Palladium on Carbon). The nomenclature "w/w" as used here means "weight of catalyst" to "weight of IAA." The catalyst was obtained from Johnson Matthey, a well-known producer of chemical catalysts in the United Kingdom. Johnson Matthey also has a United States division or subsidiary whose address is: 2001 Nolte Drive, West Deptfort, N. J. 08066-1795 (telephone: (609) 853-8000). The catalyst type used in this example is identified by Johnson Matthey as type 87L ("T87L") 5% Pd/C paste.

The solution with the catalyst was hydrogenated at 55° C. using a hydrogenation pressure of 50 psig and agitation. The solution was allowed to hydrogenate for a period of six hours. It was discovered that the hydrogenation of IAA proceeded rapidly. However, more than twice the total theoretical hydrogen was absorbed in order to convert IAA into THIAA. This indicated that perhydrogenation had occurred to produce hexahydro-iso-α-acids or octahydro-iso-α-acids. These derivative have been mentioned by others, notably Hay et al. in the 1991 J. Agric. Food Chem. article mentioned above. Consequently, it was realized that hydrogenation had to be controlled in order to realize desirable yields of THIAA.

EXAMPLE 2

A 300 gram solution of IAA in ethanol was prepared containing 90 grams of free IAA. The IAA was from the same lot as Example 1 above, i.e., 95% purity obtained from Hop Developments, Ltd. The T87L catalyst described in Example 1 (5% Pd/C catalyst) was added to the solution in an amount equal to 6.0 grams (approximately 6.7% w/w). The solution with catalyst was then hydrogenated at 50° C. using a hydrogenation pressure of 50 psig.

Rather than allow hydrogenation to be ongoing, the rate of hydrogenation absorption was carefully monitored. When the amount of absorption reached the theoretical amount required to convert IAA into THIAA, a sample of the solution was taken. Hydrogenation was then allowed to continue for a very brief period of time thereafter and was stopped completely. A second sample was taken at that time.

High-performance liquid chromatography ("H.P.L.C.") was used to determine the relative composition of each of the two samples made in this example. The chromatograms indicated that the THIAA composition of each sample was similar to the THIAA composition of samples prepared by hydrogenating an aqueous solution at a high pH. Consequently, it was concluded that it is possible to control hydrogenation to selectively hydrogenate THIAA from IAA. However, hydrogenation must be controlled by cutting off the supply of hydrogen.

EXAMPLE 3

After carrying out the process specified in Example 2 above, it was expected to achieve improved selectivity and better control of hydrogenation by using a milder hydrogenation temperature. Consequently, a third hydrogenation of a solution having the same contents and catalyst as Examples 1 and 2 was conducted with the temperature controlled to stay within the range of 25±2° C. This resulted in a reaction where hydrogen was absorbed much slower. The reaction rate proceeded at a rate approximately two thirds of the rate which took place in Example 2. Moreover, the rate of hydrogen adsorption slowed significantly before reaching the volume of gas theoretically needed to convert IAA into THIAA. This indicated that perhydrogenation to hexahydro or octahydro-iso-α derivatives was minimized at the time the supply of hydrogen was cut off. Analysis of the resultant product by H.P.L.C. confirmed that the product had the characteristics of THIAA.

TABLE 1

CATALYST TECHNICAL INFORMATION (Examples 1–3)

| | |
|---|---|
| Reference | 5R87L ("T87L") |
| Active Metal/Loading | Palladium (5%) |
| Support | Carbon Powder |
| Metal Location | Intermediate |
| Metal State | Metal |
| Surface Area | 950 m²/g |
| Metal Area | 18 m²/g |
| Mean Particle size | 20μ |
| Particle Size Distribution | 25% > 40μ   50% > 20μ |
| | 75% > 10μ   95% > 5μ |

Table 1 above sets forth the technical specifications for the T87L catalyst used in Examples 1–3. This information is published by Johnson Matthey. Example 3 indicated that it may be possible to hydrogenate IAA into THIAA in one step. However, further testing demonstrated that the conditions described in Example 3 were unlikely to lead to a commercial process to produce THIAA of the desired purity. Consequently, further tests were conducted (Examples 4–6) using a different type of Pd/C catalyst.

EXAMPLE 4

Five nearly identical experiments were carried out using a 10% Pd/C catalyst identified by Johnson Matthey as catalyst type 490 ("T490"). Each experiment involved nearly identical compositions of IAA dissolved in ethanol. The same amount of T490 catalyst was used in each experiment (5.4 grams or approximately 4.5% w/w). Hydrogenation was allowed to take place over a period of 2.25 hours, at a temperature of 25±2° C., and at a pressure of 48–60 PSIG. The following table ("Table 2") summarizes the results of these experiments and identifies (1) the amounts of IAA and ethanol used; (2) the amount of hydrogen absorbed; and (3) the weight and purity of the resultant product:

TABLE 2

| Exp. No. | Wt. Ethanol (g.) | Wt. resin isolated (g.) | Cumulative H₂ absorbed (psig units) | Wt. stripped product (g.) | UV Assay* THIAA (%) |
|---|---|---|---|---|---|
| 1. | 316 | 117.6 | 285 | 115.3 | 91 |
| 2. | 316 | 118.6 | 296 | 114.7 | 92 |
| 3. | 316 | 118.1 | 293 | 115.0 | 91 |
| 4. | 316 | 117.3 | 289 | 115.1 | 90 |
| 5. | 316 | 118.3 | 285 | 114.8 | 91 |

*Method for determination of THIAA content by UV absorbance at 250–260 nm - given in data on the product Tetralone(R) available from Kalsec.

Hydrogen absorption was monitored for each experiment. It was clear that, in each case, the solution ceased to react with hydrogen at the point where sufficient hydrogen had been absorbed to produce THIAA. Extending the reaction period, i.e., allowing hydrogenation to continue, failed to produce any significant change in the composition of the end product of hydrogenation. Preliminary H.P.L.C. analyses of the end product confirmed that they were essentially THIAA.

In Table 2, third column, the "resin" is actually a starting product consisting predominantly of IAA. It also has small amounts of other materials such as waxes or uncharacterized soft resins.

The fifth column identifies the end product that would be sold to customers. It is the starting product of the third column after hydrogenation and ethanol removal. The other materials remain in the end product.

The THIAA assay in the sixth column reflects the amount of THIAA relative to the amount of end product with the other materials remaining. In actuality, the THIAA was found to be very pure and nearly all of the IAA in the starting product was converted to THIAA.

EXAMPLE 5

The T490 catalyst used in Example 4 above was tested in subsequent experiments where hydrogenation occurred at an elevated temperature (60° C.) and the concentration level of the catalyst was varied. In one test, the T490 catalyst concentration was 4.0 percent w/w (catalyst weight to IAA weight) in a 30 percent w/w (IAA weight to ethanol weight) solution of IAA in ethanol. Hydrogenation occurred at 60° C. This same test was repeated with reduced catalyst concentrations at 3.5 percent w/w and 3.0 percent w/w, respectively. The results indicated that dropping the catalyst concentration to 3.5 percent w/w produced a marginally slower reaction, but an identical end product to that achieved at 4.0 percent w/w. When the catalyst concentration was dropped further to 3.0 percent w/w, the overall hydrogenation rate reduced to approximately ½ the rate at 4.0 percent w/w. The reaction product nevertheless remained the same, i.e., the converted products were essentially THIAA. The results indicate that hydrogenation is very efficient and naturally selective using lesser amounts of T490 catalyst.

EXAMPLE 6

Three test hydrogenations were run varying the IAA concentration. The IAA concentrations used were 15 percent w/w, 30 percent w/w, and 50 percent w/w in ethanol, respectively. The same T490 catalyst described in Examples 4 and 5 was used at a concentration of 3.5 percent w/w of the amount of IAA. Hydrogenation at 60° C. gave significantly faster hydrogen absorption rates with the higher concentration solution, without affecting the end product significantly.

TABLE 3

CATALYST TECHNICAL INFORMATION (Examples 4–6)

| | |
|---|---|
| Reference | 10R490 ("T490") |
| Active Metal | Palladium (10%) |
| Support | Carbon Powder |
| Metal Location | Intermediate |
| Metal State | Oxide |
| Water Content | 55% |
| Surface Area | 1000 m²/g |
| Mean Particle Size | 19 micron |
| Particle Size Distribution | 8% > 40μ   45% > 20μ |
| | 75% > 10μ   95% > 5μ |

Table 3 above sets forth the technical specifications for the T490 catalyst used in Examples 4–6. This information is also published by Johnson Matthey.

As shown in the specifications outlined in Tables 1 and 3, there are two significant differences between catalyst types T87L and T490. The palladium metal content of T87L is pure metal in reduced form. The T490 catalyst consists of palladium oxide.

The IAA solutions described in Examples 1–6 will have reaction inhibitors, the existence of which has long been known. These inhibitors adversely affect the functionality of Pd/C catalysts. Based on the experiments described in Examples 1–6, it is believed that T87L and T490 respond differently in the presence of the inhibitors.

It is believed that higher temperatures and larger catalyst quantities are required in connection with T87L in order to overcome the inhibitors. This would normally be expected. However, it is believed that higher temperatures tend to stimulate catalyst response such that, in combination with greater catalyst quantity, perhydrogenation occurs unless the supply of hydrogen is cut off. Consequently, if higher temperatures are used (Examples 1 and 2), one would expect that perhydrogenation can be avoided only by physically cutting off the supply of hydrogen.

Reducing the temperature does not improve the selectivity of T87L (Example 3), but it does slow the rate of hydrogenation. This makes it possible to cut off the supply of hydrogen more accurately at the point when the IAA should, in theory, be converted into THIAA. Nevertheless, the end-point of hydrogenation, or avoidance of perhydrogenation, is reached solely by cutting off the supply of hydrogen. Hydrogenation does not end naturally. Although THIAA quality was greatly improved in Example 3 over and above Examples 1 and 2, it was not considered to be satisfactory for use as a commercial process.

Although unproven at present, the response of the T490 catalyst appears to be influenced by the inhibitors so that it functions more selectively to hydrogenate IAA into THIAA. Example 4 is consistent with the use of T87L in Example 3 from the standpoint that hydrogenation occurred in both cases at a lower temperature (25°±2° C.). The resultant THIAA product in Example 4 seemed to be of high purity, which was a better result than Example 3.

It was discovered in Examples 5 and 6 that the IAA to THIAA conversion speed could be improved, and an unexpectedly cleaner hydrogenation absorption end-point occurred, when hydrogenation took place at a higher temperature (60° C.). Moreover, a lesser amount of catalyst was required.

The T87L and T490 catalysts have different supports as described in Tables 1 and 3. It is uncertain whether differences in support type have any bearing on the apparent selectivity of T490 in comparison to T87L. Instead, it is presently believed that the oxided form of Palladium used in T490 makes it more selective.

The T490 catalyst appears to be less influenced by changes in temperature when compared to T87L, at least with respect to the occurrence of perhydrogenation. It is believed that there is a slight tendency for perhydrogenation to occur if extremely high loadings of T490 are used. Nevertheless, T490 appears to provide a way to successfully hydrogenate IAA directly into THIAA without necessarily relying on hydrogen cut-off as the means for controlling the end point of hydrogenation.

It should be mentioned that describing the conversion of IAA into THIAA as being "direct" could be viewed as misleading. During the reaction, IAA are progressively reduced through intermediate forms, as hydrogenation commences, until THIAA are reached as an end point. Use of the term "direct" here should not be taken to mean that intermediate forms are in some way by-passed.

It is to be understood that the above description sets forth the best mode for carrying out the invention as it is presently known. It is possible that other variations of the invention may be discovered as it is developed further. Accordingly, what is considered to be the invention is not to be limited by the preceding description. Instead, the invention is to be limited by the following claims, the interpretation of which are to be made in accordance with the established doctrines of claim interpretation.

What is claimed:

1. A process for making THIAA, comprising:
   producing a non-buffered, natural pH, alcoholic solution of IAA;
   hydrogenating substantially all of the IAA in the presence of a noble metal catalyst, to thereby convert the IAA into high purity THIAA in a single step, wherein
   the reaction between the catalyst and the IAA selectively controls the hydrogenation of the IAA and minimizes perhydrogenation of the IAA without necessarily cutting off the supply of hydrogen.

2. The process as recited in claim 1, including hydrogenating the IAA at a temperature that is approximately 20° to 80° C.

3. The process as recited in claim 1, wherein ethyl alcohol is the solvent making up the alcoholic solution.

4. The process as recited in claim 1, wherein the noble metal catalyst includes palladium oxide.

5. A process for making THIAA, comprising:
   producing a non-buffered, natural pH, alcoholic solution of IAA; and
   hydrogenating the IAA in the presence of a noble metal catalyst, wherein the temperature of the solution is greater than 20° C., and further, the catalyst includes palladium oxide, and wherein the reaction between the catalyst and the IAA selectively controls the hydrogenation of the IAA and converts the IAA into THIAA without necessarily cutting off the supply of hydrogen.

6. The process recited in claim 5, wherein the catalyst is T490.

7. The process as recited in claim 5, including hydrogenating the IAA at a temperature that is within the range of 20° to 80° C.

8. The process as recited in claim 5, wherein the catalyst concentration relative to the IAA is within the range of to 5 percent w/w.

9. The process as recited in claim 1, wherein the catalyst concentration relative to the IAA is within the range of to 5 percent w/w.

* * * * *